United States Patent [19]

Pierre et al.

[11] 4,097,336

[45] Jun. 27, 1978

[54] REAGENT SYSTEM FOR BETA-AMYLASE ASSAY

[75] Inventors: Kenneth J. Pierre; Ker-Kong Tung; Henriette Nadj, all of Vista, Calif.

[73] Assignee: Beckman Instruments, Inc., Fullerton, Calif.

[21] Appl. No.: 758,518

[22] Filed: Jan. 11, 1977

Related U.S. Application Data

[63] Continuation-in-part of Ser. No. 657,976, Feb. 13, 1976, Pat. No. 4,036,697.

[51] Int. Cl.² ............................................. G01N 33/00
[52] U.S. Cl. ................................. 195/99; 195/103.5 C
[58] Field of Search ............................ 195/99, 103.5 C

[56] References Cited

U.S. PATENT DOCUMENTS 4,000,042  12/1976  Adams ........................ 195/103.5 C

*Primary Examiner*—Alvin E. Tanenholtz
*Assistant Examiner*—C. A. Fan
*Attorney, Agent, or Firm*—R. J. Steinmeyer; R. S. Frieman

[57] ABSTRACT

A reagent system for beta-amylase assay comprising:

a polysaccharide having glucose molecules primarily connected through alpha 1,4 linkages phosphate ions maltose phosphorylase a co-enzyme selected from a group consisting of beta-nicotinamide-adenine dinucleotide, beta-nicotinamide-adenine dinucleotide phosphate, and mixture thereof glucose-6-phosphate dehydrogenase beta-D-phosphoglucomutase mutarotase.

6 Claims, No Drawings

REAGENT SYSTEM FOR BETA-AMYLASE ASSAY

CROSS-REFERENCE TO RELATED APPLICATIONS

This application is a continuation-in-part of copending application, Ser. No. 657,976, filed Feb. 13, 1976, now U.S. Pat. No. 4,036,697.

BACKGROUND OF THE INVENTION

This invention relates to reagents and methods for determining alpha-amylase concentration in aqueous solutions such as serum and urine.

Alpha-amylase is an enzyme produced by the human body and is found in fluids such as blood, urine and saliva. It is not entirely certain what part of the body produces alpha-amylase, but it is clear that when the body is healthy, the concentration of alpha-amylase present in human fluids will vary over a range of values, and when the body is suffering from certain pathological conditions the alpha-amylase concentration will be higher or lower than the range existing when the body is healthy. For example, when a person has pancreatitis, mumps, or pancreatic cancer, the alpha-amylase concentration will be much greater than its level in the absence of such conditions. Liver diseases may produce alpha-amylase concentrations that are lower than otherwise.

Techniques for determining alpha-amylase concentrations generally involve the use of starch because of the catalytic effect of alpha-amylase on the hydrolysis of the 1,4 linkages of the amylose and amylopectin fractions of starch. If this hydrolysis is left to go to completion, the alpha-amylase will progressively degrade the starch into glucose, maltose, and oligo-saccharides. Certain techniques have attempted to correlate the decrease in the turbidity or viscosity of an aqueous starch solution after amylose hydrolysis with the resultant alpha-amylase concentration.

Other techniques utilize the quantity of reducing substances produced by the alpha-amylase-starch reaction as a measure of alpha-amylase concentration, or utilize the rate of dye release from a dyed starch by alpha-amylase as a measure of alpha-amylase concentration.

Enzymatic techniques have also been developed to measure alpha-amylase concentration by using alpha-amylase and other enzymes to hydrolyze starch into glucose which is then measured through coupled enzymatic reactions. This approach, however, is not satisfactory because of the presence in many assay specimens of glucose which will react through the coupled enzymatic reactions to produce easily detectable product in addition to that produced by enzymatic starch hydrolysis. The concentration of this endogenous glucose is generally significant with respect to the amount of glucose usually produced by the enzymatic hydrolysis technique; and as a result, such pre-existing glucose must be eliminated from the assay specimen before the assay is conducted.

Another technique is the iodometric method which utilizes the well known reaction between iodine and starch to form a blue color. When a blue colored starch-iodine solution is hydrolyzed with alpha-amylase, the blue color decreases as the alpha-amylase degrades the starch. The change in color of the blue starch-iodine solution is thus some measure of alpha-amylase concentration. This technique, however, has not been considered reliable or sufficiently definite because it is believed that the change in color does not bear a linear relationship to the concentration of alpha-amylase.

All of the foregoing techniques, while sufficient to yield a general indication of alpha-amylase concentration, are not entirely satisfactory because they either do not lend themselves to precise scientific measurements and/or are too timeconsuming.

SUMMARY OF THE INVENTION

It is therefore an object of the present invention to provide a new set of reagents and a new method for using these reagents which will overcome the problems associated with prior techniques for determining alpha-amylase concentrations.

Another object of the present invention is to provide a new procedure for determining alpha-amylase concentrations which can be performed quickly, simply, reliably and with reproducible results.

These objects are achieved by the invention disclosed and claimed hereinafter which is a novel kinetic technique for measuring alpha-amylase concentrations in aqueous solutions which is based on the following reactions:

(I) alpha-1,4 linked glucan $\xrightarrow{alpha\text{-}amylase}$ alpha-maltose + other maltooligosaccharides (II) alpha-maltose + $PO_4^\equiv \xrightarrow{MP}$ glucose + beta-D-G-1-P (III) beta-D-G-1-P $\xrightarrow{beta\text{-}PGM}$ G-6-P (IV) G-6-P + NAD $\xrightarrow{G6PDH}$ 6-P-G + NADH wherein the concentration of alpha-amylase in the aqueous solution is determined by measuring the rate of production of NADH which provides a measure of alpha-amylase concentration. The following abbreviations are employed in the above reactions and hereinafter:

ABBREVIATIONS $PO_4^\equiv$ — phosphate ion
MP — maltose phosphorylase
beta-D-G1P — beta-D-glucose-1-phosphate
beta-PGM — beta-D-phosphoglucomutase
G-1,6-diP — D-glucose-1,6-diphosphate
G-6-P — glucose-6-phosphate
6-PG — 6-phosphogluconate
G6PDH — glucose-6-phosphate dehydrogenase
6PDH — 6-phosphogluconate dehydrogenase
NAD — beta-nicotinamide-adenine dinucleotide
NADH — reduced form of beta-nicotinamide-adenine dinucleotide The reagent system of the present invention contains the starting material of reaction I, alpha-1,4 linked glucan, and all of the constituents except alpha-amylase, needed to make all of the four reactions proceed as indicated, i.e., phosphate ions, MP, beta-PGM, and G6PDH. This reagent system may be provided and used as one mixture, or it may be provided in a kit consisting of a plurality of reagents each of which contains one or more of the ingredients of the reagent system which are all mixed together when the reagents are used in the alpha-amylase assay of the invention. All of the aforesaid ingredients of said reagent system appear to be stable as one mixture and thus it is preferred that the reagent system be provided as one mixture inasmuch as it is easier to work with one reagent rather than a plurality.

EMBODIMENTS OF THE INVENTION

With respect to the first reaction employed by the present invention:

(I) alpha-1,4 linked glucan $\xrightarrow{alpha\text{-}amylase}$ alpha-maltose and other maltooligosaccharides The alpha-1,4 linked glucan may be any polysaccharide made up primarily of glucose wherein the glucose molecules are mainly connected through alpha-1,4 linkages which can be attacked by the alpha-amylase. Exemplary of such polysaccharides are starch, amylopectin, amylose, glycogen, dextrin and their degraded products, and homologs of maltooligosaccharides such as maltotriose, maltotetraose and maltopentaose or mixtures thereof.

Starch is the preferred form of said glucan because it offers the best combination of solubility, low expense, recovery and stability. Superlose 500 is the brand name of a starch which is used in the preferred embodiment of the invention. This starch has good cold water solubility, gives better response and linearity than other starches, yields good reproducibility, and is non-turbid in solution. Superlose 500 is a modified amylose distributed by Stein-Hall Company of New York City. Superlose 500 is a white, granular material having a moisture content of about 10 percent, a pH of 7, and a film tensile strength in excess of 8,000 pounds per square inch. The viscosity of Superlose 500 in Brookfield cps at 150° F is 185 for 14% solids, 55 for 10% solids, and 10 for 5% solids. At 75° F the viscosity is 2,000 for 14% solids, 275 for 10% solids, and 30 for 5% solids. Superlose 500 dissolves easily in water at room temperature in contrast to most starches which require some degree of agitation and/or heating before passing into solution. Superlose 500 is made from the modified amylose fraction of potato starch and contains no significant amount of the amylopectin fraction of starch.

GR brand starch is the brand name of another starch which may be used in the preferred embodiment. GR brand starch is distributed by E. Merck Company of 500 Executive Blvd., Elmsford, N.Y. and manufactured by Merck European of Darmstadt, Germany. This starch is dialyzed prior to use and has the following characteristics: maximum sulfate ash of 7 weight percent; 10% by weight loss on drying; 1 gram of GR starch has a reducing power equivalent to 7 milligrams of maltose; pH of between 6.5 and 7.5, and a favorable sensitivity test.

According to the present invention, it is necessary that the amount of alpha-amylase be rate-limiting. Thus, the amounts of the other constituents of the reagent system of the present invention should be present in suitable amounts to ensure that the observed reaction rate for the complete assay system is characteristic of and determined by the rate of the alpha-amylase catalyzed reaction (reaction I). For the assay of aqueous solutions of human serum or urine, it is preferred to use a concentration of between about 1.0 to about 20 grams of an alpha-1,4 linked glucan per liter of reagent. A glucan concentration of about 5 grams per liter of reagent is used in the preferred embodiment.

With regard to the second reaction employed by the present invention.

(II) alpha-maltose + phosphate $\xrightarrow{MP}$ Glucose + beta-D-Glu-1-P

The alpha-maltose produced by the first reaction is reacted with phosphate ions using maltose phosphorylase as an enzymatic catalyst to produce glucose and beta-D-glucose-1-phsophate.

The phosphate ions are supplied from any source compatible with the reagent system of the present invention. Inorganic phosphates are an example of such source. The phosphate used in the preferred embodiment is a mixture of $K_2HPO_4$ and $KH_2PO_4$ which forms a buffered solution at a pH of about 6.5 which is optimum.

The concentration of phosphate ions should be at a level to ensure that alpha-amylase is the rate-limiting compound. However, it is desirable to have not too high a concentration of phosphate ions because large concentrations may inhibit the activity of the beta-PGM enzyme. It is preferred to have about 0.01 to about 0.1 molar concentration of inorganic phosphate, with about 0.025 molar being the most preferred amount for the assay of serum.

Maltose phosphorylase is an enzyme which catalyzes the reaction of alpha-maltose and inorganic phosphate. At least about 200 International Units (IU) of this enzyme per liter of reagent is required, but about 2000 IU per liter is preferred.

The preferred source of maltose phosphorylase is a strain of the microorganism *Lactobacillus brevis* (ATCC8287) which has been cultured by Beckman Instruments, Inc., Microbics Operations of Carlsbad, Calif. and the enzyme has been extracted and purified by conventional methods therefrom. Other sources of this enzyme are strains of *Neisseria meningitides, Neisseria perflava* and other *Lactobacilli* strains.

Regarding the third reaction employed by the present invention:

(III) beta-D-Glu-1-P $\xrightarrow{beta\text{-}PGM}$ Glu-6-P

The enzyme beta-phosphoglucomutase (beta-PGM) catalyzes the conversion of beta-D-glucose-1-phosphate into Glucose-6-phosphate. Beta-phosphoglucomutase is present in at least about 100 IU per liter of reagent so that alpha-amylase of reaction I remains the rate-limiting constituent. It is preferred that about 500 IU of beta-PGM per liter of reagent be used when assaying alpha-amylase in human serum. The preferred source of beta-PGM is *Lactobacillus brevis* (ATCC8287). It is cultured and purified by conventional methods of enzyme purification. Other sources include strains of *Neisseria meningitides, Neisseria perflava* and *Euglena gracilis*.

It is preferred that glucose-1,6-diphosphate (Glu-1,6-diP) be present in the enzyme system to act as a cofactor for beta-PGM. Beta-PGM requires the beta-form of Glu-1,6-diP for activity, but it is believed that the alpha-form of this cofactor may also work. The preferred concentration of Glu-1,6-diP should be at least about 0.01 grams per liter of reagent. The optimum concentration is about 0.075 gm per liter.

It is also preferred that divalent cations selected from the class consisting of $Mn^{+2}$, $Mg^{+2}$, $Co^{+2}$, $Zn^{+2}$ or $Ni^{+2}$ be present in the enzyme system to act as a cofactor for beta-PGM. The cations $Mn^{+2}$, $Mg^{+2}$, or $Co^{+2}$ are preferred over $Zn^{+2}$ or or $Ni^{+2}$. The cation concentration should be at least about 1 millimole per liter of reagent and is preferably 8.4 millimoles per liter.

With respect to the fourth reaction employed in the present invention:

(IV) G-6-P + NAD $\xrightarrow{G6PDH}$ 6-P-G + NADH

The glucose-6-phosphate is reacted with beta-nicotinamide-adenine dinucleotide and G6PDH to produce 6-phosphogluconate and NADH.

The amount of NAD should be high enough to keep alpha-amylase the rate-limiting constituent. A suitable range for the NAD concentration is about one to about 10 millimoles per liter of reagent. The preferred concentration of NAD is about 2.5 millimoles. Beta-nicotinamide-adenine dinucleotide phosphate (NADP) may be substituted for NAD in the present invention.

The glucose-6-phosphate dehydrogenase (G-6-PDH) should also be present in a concentration of at least about 500 IU per liter of reagent so that this reaction is not the rate-limiting reaction. The preferred concentration of the G-6-PDH enzyme is about 5000 IU per liter of reagent. The preferred source of G-6-PDH is *Leuconostoc mesenteroides* (ATCC 12291) but it may be obtained from other sources.

In the preferred embodiment of the present invention, it is desirable to employ a fifth reaction as part of the assay:

(V) 6-P-G + NAD $\xrightarrow{6\text{-}PDH}$ ribulose-5-P + NADH + $CO_2$

The purpose of this fifth reaction is to increase the sensitivity and accuracy of the assay by increasing the amount of NADH produced.

The minimum concentration of 6-PDH should be at least about 200 International Units per liter of reagent. The optimum concentration of 6-PDH is about 700 International Units per liter. The preferred source of this enzyme is *Leuconostoc mesenteroides* (ATCC 12291), from which the enzyme has been cultured and purified by conventionally known methods, but it may be obtained from other sources.

Sodium chloride may be added to the reagent system to increase the activity of the alpha-amylase.

Buffers including potassium phosphate dibasic ($K_2HPO_4$) and monobasic ($KH_2PO_4$) can be used to obtain the optimum pH in which to carry out the reaction sequence. Non-phosphate buffers may be used, but are not preferred because phosphate buffers provide a source of phosphate ions. Exemplary of other buffers which were tested and found to be satisfactory are piperazine-N, N'-bis (2-ethanesolfonic acid); tris (hydroxymethyl) aminomethane; N-2-hydroxyethylpiperazine-N'-2-ethane sulfonic acid; and triethanolamine. Exemplary of other buffers which may also be satisfactory are n-(2-acetamido)iminodiacetic acid; n-(2-acetamido)-2-aminoethanesulfonic acid; and N,N'-bis(2-hydroxyethyl)-2-aminoethanesulfonic acid.

The rate of NADH production and the convention of such rate into the concentration of alpha-amylase is accomplished by known methods. One such method uses spectrophotometric means to measure the change in absorbance of light due to the production of NADH at wavelengths ranging from about 300 to about 370 millimicrons (nm) at a temperature range of from about 15° to about 50° C. A wavelength of about 340 nm at about 37° C is preferred.

When the rate of change in absorbance is measured, the concentration of alpha-amylase may be calculated by the following equation wherein the change in absorbance is measured at a wavelength of 340 nm and a temperature of 37° C:

$$IU/liter = \frac{\Delta A \times V_t \times 1000}{V_s \times 6.22}$$

$\Delta A$ = change of absorbance/minute
$V_t$ = total reaction volume
$V_s$ = volume of sample containing alpha-amylase 6.22 = millimolar absorptivity index of NADH at 340 nm

EXAMPLE 1

Ingredients of Assay Mixture for Alpha-Amylase

The following is the composition of the preferred reagent of the present invention prepared as a 1 liter solution of deionized water:

| | |
|---|---|
| Superlose 500 | 5.00 grams |
| Potassium Phosphate Dibasic | 2.65 grams |
| Potassium Phosphate Monobasic | 1.33 grams |
| Maltose Phosphorylase | 2000 IU |
| Beta-Phosphoglucomutase | 500 IU |
| NAD . $4H_2O$ | 1.8 grams |
| Glucose-6-Phosphate Dehydrogenase | 5000 IU |
| 6-Phosphogluconate Dehydrogenase | 700 IU |
| $MgCl_2$ . $6H_2O$ | 1.7 grams |
| Sodium Chloride | 0.5 grams |
| G-1,6-diP | 0.075 grams |

The pH is adjusted to about 6.0 to about 7.5 with a pH of 6.5 being preferred.

The reagent system of the present invention may be stored and used in the form of an aqueous solution or the solution may be freeze dried by conventional means and reconstituted with water when ready for use. The reagent system may also be prepared using the constituents thereof in powdered form which are solubilized with water when ready for use.

The enzyme beta-amylase, found in plants as opposed to alpha-amylase which is found in animals, catalyzes a reaction similar to the first reaction (I), hydrolyzing alpha-1,4 linked glucan to beta-maltose.

In the case of a reagent system for a beta-amylase assay the only modification to the reagent system disclosed hereinabove would be the addition of the enzyme mutarotase to catalyze conversion of beta-maltose into alpha-maltose. The kinetic beta-amylase assay therefore comprises the following simultaneous reactions:

(VI) alpha-1,4 linked glucan $\xrightarrow{beta\text{-}amylase}$ beta-maltose
(VII) beta-maltose $\xrightarrow{mutarotase}$ alpha-maltose
(II) alpha-maltose + $PO_4$ $\xrightleftharpoons{MP}$ glucose + beta-D-G-1-P
(III) beta-D-G-1-P $\xrightarrow{beta\text{-}PGM}$ G-6-P
(IV) G-6-P + NAD $\xrightarrow{G6PD}$ 6-P-G + NADH and, in a preferred embodiment, the following reaction also:

(V) 6-P-G + NAD $\xrightarrow{6\text{-}PDH}$ ribulose-5-P + NADH + $CO_2$

In the above kinetic assay for beta-amylase, it is necessary that the amount of beta-amylase be rate-limiting. The amount of the various reagents present in the beta-amylase reagent system is the same as that discussed in the case of the alpha-amylase reagent system with the only difference being the addition to said beta-amylase reagent system of at least about 2000 units, preferably about 60,000 units, of mutarotase per liter of reagent.

The principles of the instant invention may also be applied to assays for phosphatases and for inorganic phosphate by omitting the constituents of the reagent system of the present invention which make the first reaction proceed and by making the following additional modifications to the reagent system:

In the case of both the kinetic reagent system and the end-point reagent system for an inorganic phosphate assay, starch and phosphate ion are omitted from the reagent systems and maltose is added to the reagent systems. Both the kinetic inorganic phosphate assay and the end-point inorganic phosphate assay are based on the following reactions:

(II') maltose + PO$_4$ $\rightleftharpoons$ <sup>MP</sup> glucose + beta-D-G-1-P
(III) beta-D-G-1-P <sup>beta-PGM</sup> G-6-P
(IV) G-6-P + NAD <sup>G6PDH</sup> 6-P-G + NADH In a preferred embodiment of the kinetic inorganic phosphate assay, the following reaction can also be employed:

(V) 6-P-G + NAD <sup>6-PDH</sup> ribulose-5-P + NADH + CO$_2$

In the case of the end-point inorganic phosphate assay, it is necessary that maltose and NAD (and NADP, if used) be present in molar excess of the inorganic phosphate to be assayed. In the case of the kinetic inorganic phosphate assay, it is necessary that the amount of inorganic phosphate be rate-limiting.

In both the kinetic and end-point assays, the amount of phosphate ion is determined by measuring the production of NADH, NADPH, or mixtures thereof produced by the coupled enzyme reactions of the instant invention. In particular, in the case of the end-point inorganic phosphate assay, the amount of phosphate ions is determined by measuring the total quantity of NADH, NADPH, or mixtures thereof produced by the coupled enzyme reaction of the instant invention; and, in the case the kinetic inorganic phosphate assay, the amount of phosphate ions is determined by measuring the rate of production of NADH, NADPH, or mixtures thereof produced by the simultaneous coupled enzyme reactions of the instant invention.

Both the kinetic inorganic phosphate assay and the end-point inorganic phosphate assay can be run at a pH of from about 6 to about 8. Preferably, the kinetic inorganic phosphate assay is run at a pH of from about 6.5 to 8 and more preferably at a pH of about 7.4. The preferred pH for the end-point inorganic phosphate assay is about 7.0.

In both the kinetic inorganic phosphate assay and the end-point inorganic phosphate assay, the reagent system can be buffered by any non-phosphate buffer having a pH of from about 6 to about 8 and which is compatible with the reagents being used. Exemplary of such non-phosphate buffers include: piperazin-N,N'-bis(2-ethanesulfonic acid), N,N'bis(2-hydroxyethyl)-2-aminoethanesulfonic acid, triethanolamine.HCl, and tris(hydroxymethyl)aminomethane. N,N-bis(2-hydroxyethyl)-2-aminoethane-sulfonic acid is the preferred buffer for use with the kinetic inorganic phosphate reagent system and piperazin-N,N'-bis(2-ethanesulfonic acid is the preferred buffer for use with the end-point inorganic phosphate reagent system. The reagent system for the kinetic and end-point inorganic phosphate assays are set forth in examples 2 and 3, respectively.

EXAMPLE 2

Ingredients of Kinetic Assay Mixture for Inorganic Phosphate

| Ingredients | Preferred Amount | Minimum Amount Required |
|---|---|---|
| Non-phosphate Buffer | 50 mM | 10 mM |
| Maltose | 13.9 mM | 2 mM |
| Divalent Cation | 2 mM | 0 |
| Co-enzyme (NAD, NADP) | 2 mM | 0.1 mM |
| Maltose Phosphorylase | 1.6 IU/ml | 0.5 IU/ml |
| β-Phosphoglucomutase | 0.4 IU/ml | 0.1 IU/ml |
| 6-Phosphogluconate DH | 0.7 IU/ml | 0.1 IU/ml |
| Glucose-6-Phosphate DH | 5 IU/ml | 1 IU/ml |
| Glucose 1,6-diP | 0.05 mM | 0 |

EXAMPLE 3

Ingredients of End-Point Assay Mixture for Inorganic Phosphate

| Ingredients | Preferred Amount | Minimum Amount Required |
|---|---|---|
| Non-Phosphate Buffer | 50 mM | 10 mM |
| Maltose | 13.9 mM | 2 mM |
| Co-Enzyme (NAD, NADP) | 1.6 mM | 0.1 ml |
| Divalent Cation | 2 mM | 0 |
| Glucose 1,6-diP | 0.05 mM | 0 |
| Maltose Phosphorylase | 3 IU/ml | 0.5 IU/ml |
| β-Phosphoglucomutase | 0.6 IU/ml | 0.1 IU/ml |
| Glucose-6-Phosphate DH | 5 IU/ml | 1.0 IU/ml |

In the case of a reagent system for an acid phosphase assay, starch and phosphate ion are omitted from the reagent and an organic phosphate and maltose are included in the reagent. Although any organic phosphate can be used, the organic phosphate is preferably selected from a group consisting of beta-glycerophosphate, phenyl phosphate, p-nitrophenyl phosphate, α-naphthylphosphate, adenosine-3'-monophosphate, thymophthalein monophosphate, and phenolphthalein monophosphate, and more preferably is alpha-naphthylphosphate. The kinetic acid phosphatase assay therefore comprises the following simultaneous reactions:

(VIII) organic phosphate (R-PO$_4$ $\rightleftharpoons$) <sup>acid phosphatase</sup> PO$_4$ = + R
(II') maltose + PO$_4$ $\rightleftharpoons$ <sup>MP</sup> glucose + beta-D-G-1-P
(III) beta-D-G-1-P <sup>beta-PGM</sup> G-6-P
(IV) G-6-P + NAD <sup>G-6PDH</sup> 6-P-G + NADH and, in a preferred embodiment, the following reaction also:

(V) 6-P-G + NAD <sup>6-PDH</sup> ribulose-5-P + NADH + CO$_2$

In the above kinetic assay for acid phosphatase, it is necessary that the amount of acid phosphatase be rate-limiting. The organic phosphate is hydrolyzed by acid phosphatase to phosphate ion. The rate of phosphate ion release is then determined by measuring the rate of NADH, NADPH, or mixtures thereof produced utilizing the coupled enzymatic reactions of the instant invention. The pH of the acid phosphatase assay is maintained within a range of from about 4 to below 7, preferably from about 4.5 to about 6, and more preferably from about 5 to about 6. The reagent system can be buffered by any non-phosphate buffer having a pH of from about 4 to below 7 and which is compatible with the reagents being used. Exemplary of such non-phosphate buffers are sodium citrate, sodium hydrogen maleate, and sodium cacodylate. (Sodium citrate is the preferred buffer for use with the kinetic acid phosphatase reagent system). The acid phosphatase reagent system is set forth in Example 4.

EXAMPLE 4

Ingredients of Assay Mixture for Acid Phosphatase

| Ingredients | Preferred Range | Minimum Amount Required |
|---|---|---|
| Organic Phosphate | 1–5 mM | 0.5 mM |
| Maltose | 5–20 mM | 2 mM |
| Maltose Phosphorylase | 1–5 IU/ml | 0.5 IU/ml |
| β-Phosphoglucomutase | 0.3–2 IU/ml | 0.1 IU/ml |
| Co-Enzyme (NAD, NADP) | 0.2–4 mM | 0.1 mM |
| Glucose-6-phosphate DH | 2–10 IU/ml | 1 IU/ml |
| Divalent Cation | 1–5 mM | 0 |
| Glucose-1,6-Diphosphate | 0.02–0.2 mM | 0 |
| Non-Phosphate Buffer | 0.02–0.05 M | 0.01 M |

While the particular embodiment of the invention chosen herein for purposes of the disclosure is at present considered to be preferred, it is to be understood that the invention is intended to cover all changes and modifications in the disclosed embodiments which fall within the spirit and scope of the invention.

The embodiments of the invention in which an exclusive property or privilege is claimed are defined as follows:

1. A reagent system for a beta-amylase assay comprising:
   (a) a polysaccharide having glucose molecules primarily connected through alpha 1,4 linkages;
   (b) phosphate ions;
   (c) maltose phosphorylase;
   (d) a co-enzyme selected from a group consisting of β-nicotinamide-adenine dinucleotide, β-nicotinamide-adenine dinucleotide phosphate, and mixtures thereof;
   (e) glucose-6-phosphate dehydrogenase;
   (f) β-D-phosphoglucomutase; and
   (g) mutarotase;

wherein the above are present in amounts such that the beta-amylase to be assayed is rate-limiting.

2. The reagent system of claim 1 further comprising glucose-1,6-diphosphate.

3. The reagent system of claim 2 further comprising 6-phosphogluconate dehydrogenase.

4. The reagent system of claim 2 further comprising a cation selected from a group consisting of $Mn^{+2}$, $Mg^{+2}$, $CO^{+2}$, $Zn^{+2}$, $Ni^{+2}$, and mixtures thereof.

5. The reagent system of claim 2 further comprising 6-phosphogluconate dehydrogenase and a cation selected from a group consisting of $Mn^{+2}$, $Mg^{+2}$, $Co^{+2}$, $Zn^{+2}$, $Ni^{+2}$, and mixtures thereof.

6. A beta-amylase assay comprising:
   (a) performing simultaneous reactions which comprise:
      (i) reacting a polysaccharide having glucose molecules primarily connected through alpha-1,4 linkages in the presence of a beta-amylase specimen to form beta-maltose;
      (ii) reacting beta-maltose with mutarotase to form alpha-maltose;
      (iii) reacting alpha-maltose with phosphate ions in the presence of maltose phosphorylase to form glucose and beta-D-glucose-1-phosphate;
      (iv) reacting beta-D-glucose-1-phosphate in the presence of beta-D-phosphoglucomutase to form glucose-6-phosphate; and
      (v) reacting glucose-6-phosphate in the presence of glucose-6-phosphate dehydrogenase and a coenzyme selected from a group consisting of beta-nicotinamide-adenine dinucleotide, beta-nicotinamide-adenine-dinucleotide phosphate, and mixtures thereof to form the reduced form of said coenzyme and 6-phosphogluconate; and
   (b) measuring the rate of production of said reduced coenzyme, wherein the beta-amylase being measured is rate-limited.

* * * * *